United States Patent [19]

Bourland et al.

[11] Patent Number: 4,855,179
[45] Date of Patent: Aug. 8, 1989

[54] PRODUCTION OF NONWOVEN FIBROUS ARTICLES

[75] Inventors: Larry G. Bourland, Downingtown; Robert J. DiLullo, Paoli, both of Pa.; Kimberly E. Ritrievi, Florham Park, N.J.; Jon R. Valbert, Bryn Mawr, Pa.

[73] Assignee: Arco Chemical Technology, Inc., Wilmington, Del.

[21] Appl. No.: 79,312

[22] Filed: Jul. 29, 1987

[51] Int. Cl.⁴ .................. D04H 1/04; D04H 3/16
[52] U.S. Cl. .................. 428/296; 156/167; 264/6; 264/518; 264/115; 264/119; 264/236; 425/7; 425/72.2; 425/82.1; 425/83.1; 428/280; 428/288; 604/367; 604/368; 604/370; 604/372
[58] Field of Search ............ 264/518, 555, 115, 119, 264/121, 6, 12, 40.1, 40.6, 236, 347; 425/7, 72.2, 82.1, 83.1, 135, 143; 156/167; 428/296, 288, 280; 604/367, 368, 370, 372

[56] References Cited

U.S. PATENT DOCUMENTS

| 1,765,026 | 6/1930 | Miller . | |
| 2,411,660 | 11/1946 | Manning . | |
| 2,500,282 | 3/1950 | Francis . | |
| 2,681,696 | 6/1954 | Stalego | 425/7 |
| 2,988,469 | 6/1961 | Watson . | |
| 3,010,161 | 11/1961 | Duvall . | |
| 3,016,599 | 1/1962 | Perry . | |
| 3,080,611 | 3/1963 | Jarrett et al. | 156/167 |
| 3,092,531 | 6/1963 | Labino | 264/6 |
| 3,285,724 | 11/1966 | Labino | 156/167 |
| 3,357,808 | 12/1967 | Eberle . | |
| 3,442,633 | 5/1969 | Perry . | |
| 3,497,337 | 2/1970 | Denniston . | |
| 3,502,763 | 3/1970 | Hartmann . | |
| 3,670,731 | 6/1972 | Harmon . | |
| 3,755,028 | 8/1973 | Wood . | |
| 3,755,527 | 8/1973 | Keller et al. . | |
| 3,849,241 | 11/1974 | Butin et al. . | |
| 3,901,236 | 8/1975 | Assarsson et al. . | |
| 4,012,461 | 3/1977 | van Brederode | 264/12 |
| 4,100,324 | 7/1978 | Anderson et al. . | |
| 4,102,963 | 7/1978 | Wood . | |
| 4,235,237 | 11/1980 | Mesek et al. . | |
| 4,263,241 | 4/1981 | Alexandrov et al. . | |
| 4,375,447 | 3/1983 | Chung . | |
| 4,405,325 | 9/1983 | Antlfinger | 604/370 |
| 4,423,184 | 12/1983 | Kopolow et al. | 604/372 |
| 4,472,329 | 9/1984 | Muschelknautz et al. | 264/12 |
| 4,603,070 | 7/1986 | Steel et al. | 604/372 |
| 4,604,313 | 8/1986 | McFarland et al. . | |
| 4,610,678 | 9/1986 | Weisman et al. . | |
| 4,622,263 | 11/1986 | Ando et al. | 428/288 |
| 4,692,371 | 9/1987 | Morman et al. | 428/224 |

Primary Examiner—Jan H. Silbaugh
Assistant Examiner—Mary Lynn Fertig
Attorney, Agent, or Firm—Dennis M. Kozak

[57] ABSTRACT

Superabsorbent articles in the form of soft, nonwoven fibrous webs are produced from aqueous fiber-forming polymer solutions by forming the polymer into water soluble filaments, contacting the filaments with a primary air stream having a velocity effective to attenuate and to partially dry the filaments, contacting the attenuated filaments with a secondary air stream having a velocity effective to fragment the filaments into fibers and to transport the fibers to a web-forming zone while also further attenuating and drying the fibers, collecting the fibers in reticulated web-form in the web-forming zone and curing the web to a water insoluble state. The temperature and air stream velocities are controlled with respect to ambient humidity and water content of the fiber during the fiber and web formation such that the fibers are collected without sticking. Collection is preferably on a wire belt followed by transport through a curing oven to compacting rolls and web take-up.

16 Claims, 2 Drawing Sheets

PRODUCTION OF NONWOVEN FIBROUS ARTICLES

TECHNICAL FIELD

This invention relates to a process for producing superabsorbent articles in the form of soft, nonwoven fibrous webs. The nonwoven web material can be used per se or can be combined with other fibrous materials to form composites having a wide variety of applications, including diapers, sanitary napkins, incontinence products, towels, tissues, and other products for the absorption of significant quantities of fluids including body exudates and aqueous compositions of all kinds.

BACKGROUND OF THE INVENTION

The web formation process is critical in the production of all nonwoven articles. Webs are produced with a dominant fiber orientation in a known manner by textile machines such as cards or garnetts. It is also known to form webs wherein the fibers have a random arrangement by laying down on a moving wire fibers carried by a stream of an inert gas such as air. Typical processes of the latter type include the mixing of melt-blown fibers by high velocity gas streams from separate sources, as in U.S. Pat. Nos. 3,016,599, 3,502,763, 4,100,324 and 4,263,241. Other patents which use gas streams in web formation include U.S. Pat. Nos. 3,670,731, 4,235,237, 2,988,469, 4,102,963, 4,375,447, 3,755,028, 3,010,161, 2,500,282, 2,411,660 and the melt-blown fiber processes disclosed in U.S. Pat. Nos. 3,442,633, 3,497,337, 3,357,808 and 4,604,313. A wide variety of fiber types are disclosed in the foregoing patents, including natural and synthetic fibers and fibers formed from water-insoluble hydrogels including maleic anhydride copolymer gels such as disclosed in U.S. Pat. Nos. 3,901,236 and 4,610,678.

The higher the absorbency of a fiber the more difficult it is to form webs of the material having the requisite softness, flexibility and density particularly when the precursor polymer used to prepare the fibers is in solution. During the web formation process the inherent hygroscopicity of the fibers may cause the fibers to pick up water from the environment with the consequence that if the fibers are over-dried during the process, voids will form in the web and the web will crack. On the other hand, if the fibers are over-wet the web will become brittle during a subsequent curing operation. The resulting web in both cases will have poor integrity and lack the density, softness and flexibility desired.

SUMMARY OF THE INVENTION

A process has now been found which combines fiber and web formation in such manner that superabsorbent nonwoven webs can be produced, batch-wise but preferably continuously, wherein conditions are controlled to provide uniform density (desirably of about 30-200 g/m$^2$), integral but random fiber distribution, and the flexibility and softness important for use of the webs in water absorbent personal care products. The superabsorbency of the webs is demonstrated by their ability to absorb many times their weight of water and aqueous solutions, on the order of 40 to 1000 grams of water or aqueous solution per gram of web material under free swelling conditions and to retain similarly large quantities of aqueous fluids under pressure. "water" and "aqueous fluids" is herein intended to mean and include not only water per se but also electrolyte solutions, body fluids and aqueous solutions of all kinds.

In one aspect of the invention, nonwoven fibrous webs are produced from an aqueous solution of a fiber-forming polymer composition which initially is water soluble but becomes water insoluble and superabsorbent upon curing, wherein the polymer solution is formed into filaments, the filaments are contacted with a primary air stream having a velocity effective to attenuate the filaments, the attenuated filaments are contacted in a fiber-forming zone with a secondary air stream having a velocity effective to further attenuate and to fragment the filaments into fibers and to transport the fibers to a web-forming zone, the fibers are collected in reticulated web form in the web-forming zone, and the web is cured. Each air stream also evaporates water from the filaments and fibers (the secondary air stream more so than the primary air stream), the fibers thereby being dried to the extent that they will collect and cure to a soft web without substantially flowing or sticking together.

In another aspect, nonwoven web-producing apparatus is provided, comprising the combination of means for forming an aqueous polymer solution into filaments, first air supply means positioned to direct an air stream upon and to partially attenuate and dry the filaments, a housing having opposing inlet and outlet means, second air supply means positioned to direct an air stream upon the filaments for further attenuation and for fragmentation thereof, and to further dry and to carry the filaments through the inlet and outlet of the housing, a foraminous surface at the outlet of the housing for collecting the fragments in web form, suction means adjacent to the foraminous surface to entrain the fragments on the surface, and means for curing the web on the foraminous surface.

Other aspects of the invention include a nonwoven web-producing process wherein the polymer composition from which the fibers of the web are produced is a carboxylic polymer cross-linked by hydroxyl or heterocyclic carbonate functionality, and the nonwoven web produced by the process.

These and other aspects, features and advantages of the invention will be apparent from the drawings and specification which follow.

DETAILED DESCRIPTION

Figure 1:
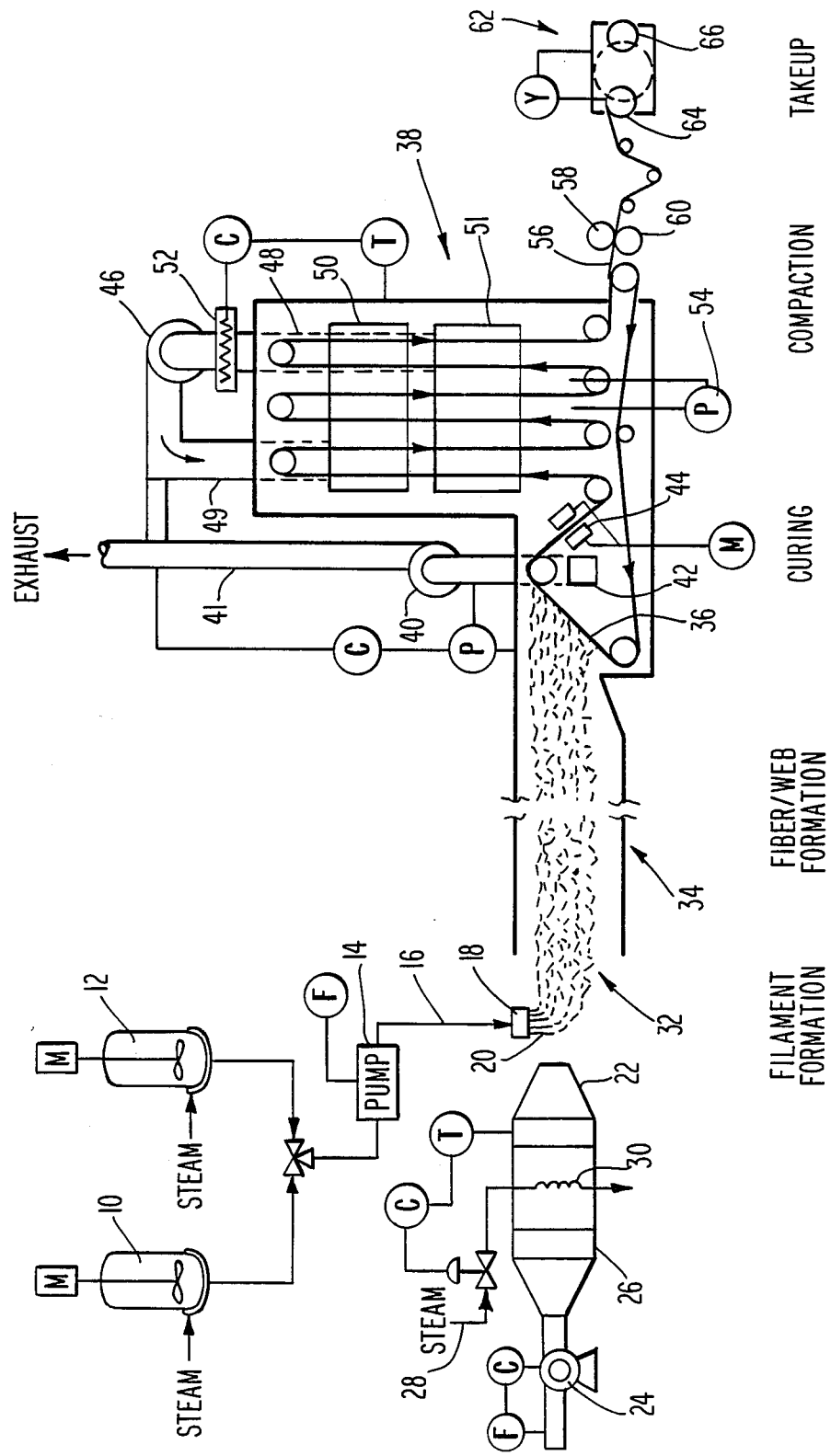
FIG. 1 is a schematic of apparatus useful in the process of the invention and includes identification of the major steps of the process.
Figure 2:
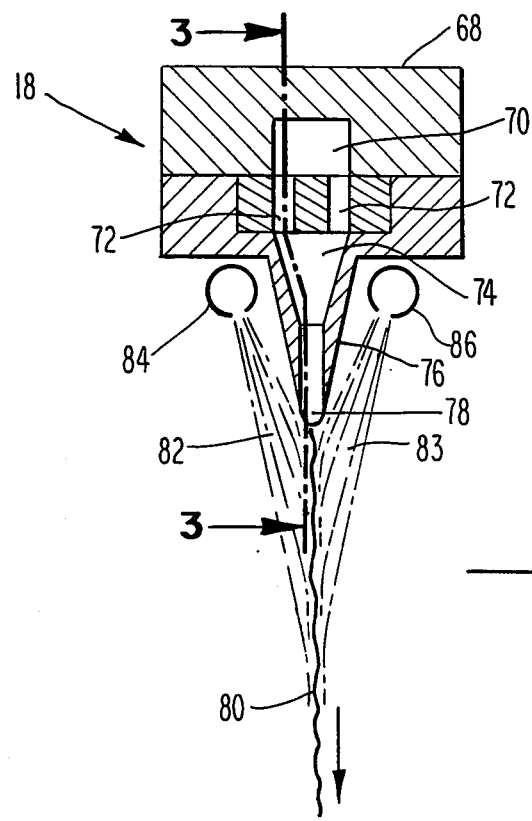
FIG. 2 is a vertical section of one embodiment of an extrusion die useful in the filament formation step of the process.
Figure 3:
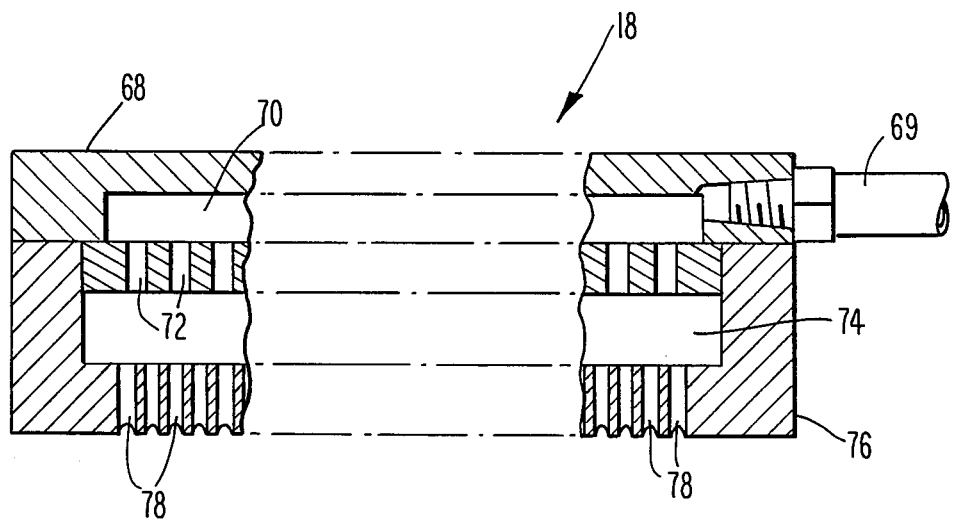
FIG. 3 is a vertical section along the line 3—3 of FIG. 2 showing other structure of the extrusion die of FIG. 2.

With reference to FIG. 1 of the drawings, in the filament forming step of the invention a hydrophilic polymer solution supplied from one or more feed tanks, such as steam-heated and motor (M)-agitated polymer feed tanks 10 and 12, is pumped by pump 14 having a flow control (F) via line 16 to filament forming means such as an extrusion device 18. The extrusion device may have any suitable design including one or more nozzles, spinnerets or die openings. FIGS. 2 and 3 illustrate one embodiment of extrusion device in the form of a die (described in detail below). The viscosity of the polymer solution is regulated by the solids content of the polymer composition feed stock and temperature thereof for an efficient rate of extrusion. Heating the polymer feed up to about 200° F. as necessary is accomplished by steam jackets or other means. For example, at a solids concentration of about 25-60%, preferably about 35-55% and an extrusion device comprising a bank of nozzles with openings of 0.028 inch diameter, a suitable extrusion rate is about 2.5 grams per minute per nozzle at room temperature (ca.70° F.). If the extrusion device includes a die having, for example, a length of about 3-10 inches and 6-12 holes per inch, the holes being evenly spaced and 0.020 inches in diameter, a suitable extrusion rate is about 0.5 to 5 grams per minute per hole at room temperature. Of course, the extrusion rate will also depend upon the type and character of the polymer composition, particularly its viscosity.

While hydrophilic thermosetting and thermoplastic polymer compositions of all types may be used in the process, such as the polymer types described in the patents cited above (the disclosures of which are incorporated herein by reference), the process has particular applicability to filament and web formation from a polymer composition comprising a blend of (1) a copolymer of at least one alpha, beta-unsaturated carboxylic monomer and at least one monomer copolymerizable therewith, and (2) a cross-linking agent having crosslinking functionality comprising hydroxyl or heterocyclic carbonate groups. More particularly, the polymer composition is a blend of a copolymer of the foregoing type having about 20-80 weight percent pendant carboxylic acid groups and about 80-20 weight percent pendant carboxylate groups, and a suitable hydroxyl or O-heterocyclic carbonate-containing crosslinker.

The copolymer of the polymer composition may contain about 25-75 mole percent recurring units of at least one alpha, beta-unsaturated monomer bearing at least one pendant unit selected from carboxylic acid units and derivatives of carboxylic acid units, and about 75-25 mole percent recurring units of at least one monomer copolymerizable therewith, wherein about 20-80 mole percent of the total pendant units introduced through the recurring alpha, betaunsaturated monomer units are carboxylic units or which are converted into carboxylic acid units, and wherein about 80-20% of the total pendant units are carboxylate salt units or which are converted into carboxylate salt units. Preferably, the copolymer will contain about 35-65 total mole percent of recurring units of at least one alpha, betaunsaturated monomer and about 65-35 total mole percent of at least one copolymerizable monomer. More preferably, the comonomers of the copolymer will be present in equimolar proportions.

Suitable hydroxyl-containing crosslinking units include one or more compounds having at least two hydroxyl groups, such as alkylene glycols of 2-10 carbon atoms and ethers thereof, cyclic alkylene glycols, bisphenol A, hydroxy alkylene derivatives of bisphenol A, hydroquinone, phloroglucinol, hydroxy alkylene derivatives of diphenols, glycerol, erythritol, pentaerythritol, monosaccharides and other compounds specified hereinafter.

Suitable, alpha, beta-unsaturated monomers are those bearing at least one pendant carboxylic acid unit or derivative of a carboxylic acid unit. Derivatives or carboxylic acid units include carboxylic acid salt groups, carboxylic acid amide groups, carboxylic acid imide groups, carboxylic acid anhydride groups and carboxylic acid ester groups.

Typical alpha, beta-unsaturated monomers useful in the invention include maleic acid, crotonic acid, fumaric acid, mesaconic acid, the sodium salt of maleic acid, the sodium salt of 2-methyl, 2-butene dicarboxylic acid, the sodium salt of itaconic acid, maleamic acid, maleamide; N-phenyl maleimide, maleimide, maleic anhydride, fumaric anhydride, itaconic anhydride, citraconic anhydride, methyl itaconic anhydride, ethyl maleic anhydride diethylmaleate, methylmaleate, and the like, and any mixtures thereof.

Any suitable copolymerizable comonomer can be employed. Suitable copolymerizable comonomers include ethylene, propylene, isobutylene, $C_1$ to $C_4$ alkyl (meth)acrylates, vinyl acetate, methyl vinyl ether, isobutyl vinyl ether, and styrenic compounds having the formula:

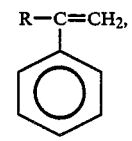

wherein R represents or an alkyl group having from 1 to 6 carbon atoms and wherein the benzene ring may be substituted with low molecular weight alkyl or hydroxy groups.

Typical $C_1$ to $C_4$ alkyl acrylates include methyl acrylate, ethyl acrylate, isopropyl acrylate, n-propyl acrylate, n-butyl acrylate, and the like, and any mixtures thereof. Suitable $C_1$ to $C_4$ alkyl methacrylates include methyl methacrylate, ethyl methacrylate, isopropyl methacrylate, n-propylmethacrylate, n-butyl methacrylate, and the like, and any mixtures thereof. Suitable styrenic compounds include styrene, alpha-methylstyrene, p-methylstyrene, t-butyl styrene, and the like, and any mixtures thereof.

The pendant units on the alpha, beta-unsaturated monomer, will determine what, if any, additional reactions must be carried out to obtain a copolymer having the requisite pendant units necessary to produce water-absorbing polymer compositions useful in the invention having about 20-80 percent pendant groups such as carboxylic acid units and about 80 to about 20 percent pendant carboxylate salt units. Preferably, both units are present in an amount of from about 30 to about 70 percent.

In general, if the alpha, beta-unsaturated monomer bears only carboxylic acid amide, carboxylic acid imide, carboxylic acid anhydride, carboxylic acid ester groups, or mixtures thereof, it will be necessary to convert at least a portion of such carboxylic acid derivative groups to carboxylic acid groups by, for example, a hydrolysis reaction. If the alpha, beta-unsaturated monomer bears only carboxylic acid salt groups, acidification to form carboxylic acid group will be necessary.

Similarly, the final copolymer must contain about 80-20 percent pendant carboxylate salt units. Accordingly, it may be necessary to carry out a neutralization reaction Neutralization of carboxylic acid groups with a strong organic or inorganic base such as NaOH, KOH, ammonia, ammonia-in-water solution, or organic amines will result in the formation of carboxylate salt units, preferably carboxylate metal salt units.

The sequence and the number of reactions (hydrolysis, acidification, neutralization, etc.) carried out to obtain the desired functionality attached to the copolymer backbone are not critical. Any number and sequence resulting in a final copolymer which possess about 20-80 percent pendant carboxylic acid units and about 80-20 percent pendant carboxylate salt units is suitable.

One copolymer particularly suitable for use in forming superabsorbent webs in accordance with the invention is a copolymer of maleic anhydride and isobutylene. Another is maleic anhydride and styrene. Suitable copolymers will have peak molecular weights of from about 5,000 to about 500,000 or more. The copolymers of maleic anhydride and isobutylene and/or styrene can be prepared using any suitable conventional methods. Maleic anhydride/isobutylene copolymers are also commercially available from Kuraray Isoprene Chemical Company, Ltd., Tokyo, Japan, under the trademark ISOBAM. ISOBAM copolymers are available in several grades which are differentiated by viscosity molecular weight: ISOBAM-10, 160,000 to 170,000; ISOBAM-06, 80,000 to 90,000; ISOBAM-04, 55,000 to 65,000; and ISOBAM-600, 6,000 to 10,000.

To produce water-absorbing polymer compositions useful in the invention, at least one copolymer as described about and at least one crosslinking compound bearing at least two hydroxyl or heterocyclic carbonate groups are blended such that the waterabsorbing composition contains in weight percent about 80-99.5 total copolymer and about 0.5-20 total crosslinking compound. Preferably, the composition will contain about 90-99 weight percent total copolymer and about 1-10 weight percent total crosslinking agent.

Any suitable organic compound bearing at least two hydroxyl or heterocyclic carbonate groups and having a relatively low molecular weight, less than 1,000, can be employed as a crosslinking agent for the copolymers.

Suitable crosslinking compounds include ethylene carbonate, propylene carbonate, 1-2 butylene carbonate, 2-3 butylene carbonate, phenyl ethylene carbonate, ethylene glycol, propylene glycol, trimethylene glycol, 1,4-butane diol, 2-methyl-1, 3-propane diol, neopentyl glycol, 1,5-pentane diol, diethylene glycol, dipropylene glycol, 1,4-cyclohexane dimethanol, Bisphenol A, 1,4-bis-(beta-hydroxyethoxy) bisphenol, hydroquinone, phlorogl ucinol, glycerol, erythritol, pentaerythritol, meso-erythritol, 1,7-dihydroxysedoheptulose, sucrose, natural monosaccharides, and the like, including any mixtures thereof.

In the filament forming step (again, with reference to FIG. 1), the polymer filament 20 is contacted with a primary air stream directed generally vertically from nozzles, openings in horizontally positioned tubes or other means as it leaves the extruder 18. The air is supplied by a compressor blower (operating up to about 25 psi) or other suitable source. The velocity of the air stream is selected to partially dry and attenuate the filaments to a diameter sufficiently small such that the filaments will be further attenuated and will fragment easily when contacted with a secondary air stream from nozzle 22 supplied from a blower 24 through a chamber 26. Blower 24 may be provided with a suitable controller (C) and flow indicator (F). A primary air stream velocity (measured 6 inches from the air exits) of at least about 500 feet per minute (fpm), e.g., about 500-8,000 fpm, will be effective. The secondary air temperature in tunnel 34 may be regulated by steam flow in line 28 to a heat exchanger 30 in chamber 26. A conventional temperature sensor (T) and controller (C) regulates the temperature through a suitable control valve and control valves actuator as shown. Filaments 20 will have diameters of about 5-20 microns as a result of the entrainment and attenuation by the primary air stream.

When contacted by the high velocity secondary air stream from nozzle 22, flowing at a velocity of at least about 3,000 feet per minute, e.g., about 3,000 to 10,000 feet per minute or greater, the filaments 20 are further attentuated and dried, and are fragmented into fiber pieces 32 which are carried by the secondary air and vaporized water through the housing or tunnel 34 having an inlet adjacent the nozzle 22 and an opposing outlet. The fibers then deposit on a foraminous collector surface such as a screen 36 positioned in the outlet of the tunnel. Screen 36 preferably is mounted or positioned at an angle to the longitudinal axis of tunnel 34, eg., about 45°. The temperature and humidity in the tunnel 34 are sensed and regulated such that the water content of fragments 32 as they collect on screen 36 is about 10-15 percent by weight. If the fiber fragments are over-dried at this point the resulting web will contain voids and subsequently crack during the curing step. If the fibers are too moist the web will become brittle during the subsequent curing. The secondary air stream in addition to fragmenting and drying the fibers, augments the attenuation of the fibers to the desired 5-20 micron diameter range.

Tunnel 34 is dimensioned to attain the proper moisture content in the fibers as they collect on screen 36. A tunnel housing about 12 feet long and having interior dimensions of about 3 feet by 3 feet is suitable but other dimensions will be effective depending upon the water content of the polymer composition as it is formed into filaments, the hydroscopicity of the polymer composition, and the extent to which the polymer composition is neutralized and crosslinked. Passage of the fibers through the tunnel as well as temperature and humidity control is facilitated by lining the tunnel with suitably surfaced insulating material, such as glass fiber batting surfaced with a water impervious film. While nozzle 22 and tunnel 34 are shown horizontally positioned in FIG. 1, vertical or other positioning may also be practiced.

Collection of the fiber fragments 34 on the screen 36 is facilitated by a suction generated by a blower 40 which pulls secondary air from tunnel 34 through an exhaust chamber 42. The suction also minimizes condensation of water on the interior walls of tunnel 34. The differential pressure of the suction generated by blower 40 is regulated by a controller (C) and measured by a pressure sensor (P) across the screen 36. The suctioned air is exhausted through a stack 41 and thereby also creates a pressure differential to hold the web in place on the screen 36 during initial passage into the oven 38.

Although screen 36 may comprise a fixed surface or a rotating drum separate from the tunnel 34, preferably screen 36 is a foraminous wire or wire mesh belt as shown, which moves continuously through a curing oven 38. Moisture sensors 44 having a readout M determine whether the fibrous material on the wire has the requisite moisture content as it enters the oven. Typically, the moisture should be less than 20% by weight as the material enters the oven, to prevent the fibers from flowing and sticking together, thereby losing fiber integrity. The fiber fragments now collected on the wire in web form are maintained on the wire during passage through the oven by air pressure against one side of the wire and suction from the other side generated by air cycled by a blower 46 from a suction conduit 48. The air is transported via a supply conduit 49 to a distribution region 50 subdivided into chambers or manifolds (not shown) positioned on one side of each of the vertical wires shown in FIG. 1. Air thus suctioned through one face of the wire is collected in an exhaust region 51 adjacent the opposing face of the wire to complete the air flow cycle. A heater 52 desirably is mounted upstream of blower 46 to heat the air stream as required for curing of the web. Suitable temperature controls (T,C) are provided to relate air temperature in the oven to speed of the wire and other parameters for efficient cure. The air pressure across wire 36 is measured by a sensor 54. Any design of curing oven, and air supply and exhaust system of the curing oven, suitable for obtaining efficient cure can be used. One such design is the oven and air distribution system commercially available from Honeycomb Systems, Inc., of Biddeford, Me.

An oven temperature of about 250° C. for about 5 minutes residence time or about 270° C. for about 2.5 minutes residence time provides good cure but lower temperatures and longer residence times are also suitable, such as about 210° C. for about 20 minutes. Higher temperatures can be used with concomitantly lower residence times provided the webs do not discolor. Generally, the oven temperature range may be about 150°–275° C. for residence times of about 35–0.5 minutes.

Upon emerging from the curing oven, product web 56 desirably is compacted by any suitable means such as nip rolls 58 and 60, and is transported to a take-up station 62 where it is wound on an idler spool 64 driven by spool 66. A tension controller (Y) regulates take-up tension in a known manner. If desired, embossing rolls may be used for the compaction to improve the integrity and appearance of the web by decreasing the visibility of small dis-continuities in the web.

FIGS. 2 and 3 illustrate one embodiment of a die suitable in forming the filaments in extrusion device 18. With reference thereto, a die head comprises a die head cover 68, one or more entry conduits 69, and a chamber 70 defining a manifold for entry of polymer syrup through channels 72 to nozzle feed chamber 74. The nozzle chamber is defined by tip body 76 and communicates with die holes 78. Filaments 80 are thus extruded and entrained by primary air streams 82 and 83 injected from openings in supply tubes 84 and 86. Suitable air supply tubes may be about 10 inches long and have 12 holes per inch wherein the hole diameter is 0.020 inch. The velocity and angles of impingement of air streams 82 and 83 upon filament 80 are selected relative to the viscosity of the polymer syrup and the location of the secondary air stream such that filaments 80 will be entrained and attenuated to the desired diameter range A. A suitable angle of impingement is 20 degrees. An air knife may be used in place of tubes 84 and 86, if desired.

Thus by practice by the process of the invention, superabsorbent webs of uniform density and having the requisite softness and flexibility are produced continuously and efficiently. The resulting web is dry to the touch and can be conveniently incorporated into various product forms in accordance with well-known procedures.

The following examples will serve, in conjunction with FIGS. 1–3, as further illustration of the invention.

EXAMPLE 1

A polymer syrup is prepared, comprising a 40% polymer solids solution of a maleic anhydride/isobutylene copolymer having a viscosity average molecular weight of about 160,000–170,000 and which is 50% neutralized with sodium hydroxide and crosslinked with 7 phr of propylene carbonate per (7 parts by weight of propylene carbonate per 100 parts by weight of copolymer).

A continuous web is produced by blowing fibers fragmented from filaments extruded from the polymer syrup through a die (such as die 18 of FIGS. 2 and 3) using primary air and secondary air as described hereinabove, to a web forming screen 36 comprising a wire mesh belt which travels through a curing oven 38. The polymer feed pump rate (Nichol-Zenith Pump, Model BLB-5456-30 cc/rev.) is set at 3 rpm, for extrusion of polymer at 100 gm/minute or at 2.6 gm/minute/hole in the die. The belt speed is set at 2.5 feet per minute. The relative polymer feed and wire speed are matched to give the desired web density. The required oven temperature is then set to completely cure the web in the residence time of the web in the heated zone of the curing oven. For an oven 63 feet long and a belt of 2.5 fpm, the cure time is 25 minutes. For this residence time, 195° C. is a suitable oven temperature. Once the polymer is flowing freely through the die, the belt is moving, and the proper oven temperature is reached, the primary air is turned on to reach a velocity of about 8000 fpm through the holes in the air tubes 84 and 86 of FIG. 1. Then, the secondary air is turned on to at least 7000 fpm for this feed rate and the air is heated to 125° C. The temperature of the secondary air is adjusted in chamber 26 to dry the web as it is formed to 10–15 wt. % moisture. The secondary and primary air are removed in the oven 38 through the belt and exhausted to the outside by exhaust blower 40 and suction box 42 behind the belt. One inch of water pressure drop across the web and belt is sufficient to exhaust the air and deposit the fibers in web form on the belt. The exhaust fan speed is increased until the pressure drop is achieved. The web travels through the oven on the moving belt and is removed at the exit where it can be embossed or simply rolled up. A web produced as described has a density of 105 g/m$^2$, absorbs 40.2 g/g of 0.9% brine solution and retains 26.3 g/g of the brine solution under a pressure of 0.5 psi. The water-swelled web is dry to the touch.

EXAMPLE 2

Substantially as described in Example 1 but using a polymer formulation differing from that of Example 1 by substitution of pentaerythritol and butanediol for propylene carbonate in amounts of 8 phr and 2 phr, respectively, and increasing the belt speed to 2.8 fpm, a fibrous web is produced. The cure residence time is 22.5 minutes. The oven temperature for this formulation and residence time is 175° C. and the secondary air temperature is 100° C. The collector pressure drop on the belt is increased to 2.0 inches of water to draw the fibers to the belt more evenly. The web produced has a density of 83 g/m$^2$, absorbs 48.8 g/g of a 0.9% brine solution and retains 28.9 g/g of the brine solution under a pressure of 0.5 psi. The solubility of the polymer is 14.6%.

We claim:

1. A process for producing a nonwoven fibrous web from an aqueous solution of a polymer composition which is water insoluble and superabsorbent upon curing, which comprises:
- (a) forming the polymer solution into water soluble filaments,
- (b) contacting the filaments with a primary air stream having a velocity effective to partially attenuate and to partially dry the filaments,
- (c) contacting the filaments in a fiber-forming zone with a secondary air stream having a velocity effective to further attenuate and to fragment the filaments into fibers, to further dry the fibers and to transport the fibers to a web-forming zone,
- (d) collecting the fibers in reticulated web-form in the web-forming zone, and
- (e) curing the web in a curing zone;

wherein the temperature and air stream velocities are controlled with respect to ambient humidity and water content of the fiber during fiber and web formation such that during collection the fibers remain substantially non-sticking and cure in the curing step to a soft, integral web.

2. The process of claim 1 wherein the fibers formed from the polymer solution are collected on a forming wire and the forming wire carrying the fibers moves continuously through the curing zone.

3. The process of claim 1 including (f) compacting the cured web.

4. The process of claim 3 wherein the compacting includes embossing the web.

5. The process of claim 1 wherein the temperature and air stream velocities are controlled in the fiber-forming and web-forming zones whereby the moisture content of the fibers prior to curing is less than 20% by weight.

6. The process of claim 1 wherein the primary air stream entrains and transports the filaments to the fiber forming zone.

7. The process of claim 1 wherein the velocity of the primary air is at least about 500 fpm and the velocity of the secondary air is at least about 3000 fpm.

8. The process of claim 1 wherein the polymer solution comprises about 25 to 60% polymer solids and the polymer composition comprises a blend of (1) a copolymer of at least one alpha, beta-unsaturated carboxylic monomer and at least one monomer copolymerizable therewith and (2) a crosslinking agent wherein the crosslinking functionality is selected from hydroxyl or heterocyclic carbonate groups.

9. The process of claim 8 wherein the copolymer comprises about 20–80 weight % pendant carboxylic acid groups and about 80–20 weight % pendant carboxylate groups.

10. The process of claim 8 wherein the copolymer is a copolymer of maleic anhydride and styrene, isobutylene, or a mixture of styrene and isobutylene, and the crosslinking agent is propylene carbonate, ethylene glycol, propylene glycol, 1,4-butanediol, diethylene glycol, glycerol, pentaerythritol, mesoerythritol or any mixture thereof.

11. The process of claim 1 wherein the polymer solution comprises about 25 to 60% polymer solids, the polymer composition comprises a blend of (1) a copolymer of at least one alpha, beta-unsaturated carboxylic monomer and at least one monomer copolymerizable therewith, and (2) a crosslinking agent, wherein the crosslinking functionality is selected from hydroxyl or heterocyclic carbonate groups, and the process conditions are as follows:
  primary air velocity: about 500 to 8000 fpm; secondary air velocity: at least about 3000 fpm; secondary air temperature: about 25° to 140° C. temperature of curing zone: about 150° to 275° C. residence time of web in curing zone: about 0.5 to 35 minutes.

12. The process of claim 1 wherein the polymer solution comprises about 35 to 55% polymer solids, the polymer composition comprises a blend of (1) a partially neutralized copolymer of maleic anhydride and styrene, isobutylene, or a mixture of styrene and isobutylene, and (2) a crosslinking amount of propylene carbonate, ethylene glycol, propylene glycol, 1,4-butanediol, diethylene glycol, glycerol, pentaerythritol, meso-erythritol or any mixture thereof, and the process conditions are as follows:
  primary air velocity: about 500 to 8000 fpm; secondary air velocity: at least about 3000 fpm; secondary air temperature: about 25° to 140° C. temperature of curing zone: about 150° to 275° C. residence time of web in curing zone: about 0.5 to 35 minutes.

13. The nonwoven web produced by the process of claim 1.

14. The nonwoven web produced by the process of claim 8.

15. The nonwoven web produced by the process of claim 10.

16. The nonwoven web produced by the process of claim 12.

* * * * *